United States Patent
Chen et al.

(10) Patent No.: US 11,254,906 B2
(45) Date of Patent: Feb. 22, 2022

(54) AUTOMATIC PURIFICATION SYSTEM AND BIOLOGICAL SAMPLE PURIFICATION METHOD

(71) Applicant: Nanjing GenScript Biotech Co., Ltd., Nanjing (CN)

(72) Inventors: Xin Chen, Nanjing (CN); Ruina He, Nanjing (CN); Chao Wang, Nanjing (CN); Hong Qian, Nanjing (CN); Tao Bai, Nanjing (CN)

(73) Assignee: Nanjing GenScript Biotech Co., Ltd., Jiangsu (CN)

( * ) Notice: Subject to any disclaimer, the term of this patent is extended or adjusted under 35 U.S.C. 154(b) by 197 days.

(21) Appl. No.: 16/475,873

(22) PCT Filed: Jan. 4, 2018

(86) PCT No.: PCT/CN2018/071401
§ 371 (c)(1),
(2) Date: Jul. 3, 2019

(87) PCT Pub. No.: WO2018/127102
PCT Pub. Date: Jul. 12, 2018

(65) Prior Publication Data
US 2019/0376022 A1    Dec. 12, 2019

(30) Foreign Application Priority Data

Jan. 4, 2017   (CN) .......................... 201710005879.2

(51) Int. Cl.
*C12M 1/00*      (2006.01)
*B03C 1/033*    (2006.01)
(Continued)

(52) U.S. Cl.
CPC ........... *C12M 47/12* (2013.01); *B03C 1/0332* (2013.01); *B03C 1/0335* (2013.01); *B03C 1/288* (2013.01);
(Continued)

(58) Field of Classification Search
None
See application file for complete search history.

(56) References Cited

U.S. PATENT DOCUMENTS 3,970,518 A  *  7/1976  Giaever ................. A61K 39/44
                                                                    435/239
5,508,164 A  *  4/1996  Kausch ............. C12N 15/1006
                                                                    435/6.16
(Continued)

FOREIGN PATENT DOCUMENTS

| CN | 101671631 A | 3/2010 |
| CN | 101735937 A | 6/2010 |
| CN | 203530328 U | 4/2014 |

OTHER PUBLICATIONS

International Search Report and Written Opinion dated Apr. 12, 2018 for PCT/CN2018/071401, with English translation of ISR (11 pages).

*Primary Examiner* — David C Mellon
(74) *Attorney, Agent, or Firm* — Klarquist Sparkman, LLP

(57) ABSTRACT

An automatic purification system using magnetic particles comprises: 1) a first container module; and 2) a system controller module. The first container module comprises a first container and a first magnetic field supply device disposed outside the first container. A first container liquid inlet is formed in the upper portion of the first container, and a first container liquid outlet is formed in the bottom of the first container. The system controller module can generate a variable magnetic field in the first container by controlling (Continued)

the first magnetic field supply device. A method for purifying a target component from a biological sample comprises a step for allowing a biological sample containing a target component to be in contact with magnetic particles capable of specifically binding the target component, in the first container in the automatic purification system. The automatic purification system and method help to efficiently separate a target product from a biological sample, and helps to reduce process costs and time at the same time.

20 Claims, 3 Drawing Sheets

(51) Int. Cl.
   *B03C 1/30* (2006.01)
   *B03C 1/28* (2006.01)
(52) U.S. Cl.
   CPC ............ *B03C 1/30* (2013.01); *B03C 2201/18* (2013.01); *B03C 2201/26* (2013.01)

(56) References Cited

U.S. PATENT DOCUMENTS

| | | | | |
|---|---|---|---|---|
| 5,681,478 | A | * | 10/1997 | Lea .......................... C12Q 1/24 |
| | | | | 210/695 |
| 5,691,208 | A | * | 11/1997 | Miltenyi ............. A61M 1/3603 |
| | | | | 436/526 |
| 2012/0132593 | A1 | | 5/2012 | Murthy et al. |
| 2020/0030816 | A1 | * | 1/2020 | Kronshage ............ B03C 1/0335 |

* cited by examiner

AUTOMATIC PURIFICATION SYSTEM AND BIOLOGICAL SAMPLE PURIFICATION METHOD

CROSS REFERENCE TO RELATED APPLICATIONS

This is the U.S. National Stage of International Application No. PCT/CN2018/071401, filed Jan. 4, 2018, which in turn claims the benefit of China Patent Application No. 201710005879.2, filed Jan. 4, 2017.

TECHNICAL FIELD

The present application relates to a purification system, in particular to an automatic purification system for purifying a target component from a biological sample. The present application also relates to a method for purifying a target product by using the system.

BACKGROUND ART

In the course of an industrial production, the production of a main product is inevitably accompanied by by-products. While the production flow and process can be optimized constantly, and the proportion of the main product in the total products can be continuously increased, there are necessarily some by-products. Therefore, purification of the main product by separation is an essential step in the whole production process.

Purification by separation is mainly to make use of the differences in physical properties or chemical properties of various components in a mixture to separate a target component from other components through appropriate devices or methods, thus achieving the purpose of purifying the target component. A commonly used method is carrier method, which utilizes a specific binding region carried on the carrier to specifically bind to the component to be separated, thus separating the component to be separated from the mixture and achieving product purification.

Carrier matrices used in conventional apparatuses for purification by separation are generally polymers (such as agarose, polystyrene, etc.), which have the function to be used for purification by separation by being made to have specific binding regions on their surfaces.

A general process of the carrier method is as follows:

1. Filtration. As the carrier is mostly porous, if there are insoluble particles in a sample or the sample has a relatively high viscosity, such substances need to be removed to avoid pore blockage.

2. Concentration. If the concentration of a component to be separated in the sample is too low, the sample needs to be enriched and concentrated to improve efficiency.

3. Loading. After the two steps mentioned above, the sample can be completely passed through the carrier in a certain way. In this step, the component to be separated is bound to the carrier, and the remaining components flow out of the carrier.

4. Washing impurities. In step 3, in addition to the component to be separated, actually some of the other components may also bind to the carrier non-specifically, but with binding forces being much weaker than that of the component to be separated to the carrier, and they can be washed off the carrier by corresponding reagents, while the component to be separated continues to bind to the carrier.

5. Elution. In this step, the component to be separated can be separated from the carrier by a corresponding reagent and then collected.

6. Removal of impurities and concentration. In step 5, the eluting reagent may introduce unnecessary impurities into the component to be separated, and further purification by separation is required as needed. According to requirements for final product, the purified product needs to be concentrated.

7. Regeneration of carrier. The carrier after step 5 needs to be retreated, so that it can be reused to save costs.

In an industrial production, if the component is a relatively single one, step 5 may be omitted by selecting a carrier that binds by-products, thus shortening the production process.

In current industrial production, the carrier method is a relatively common method. However, after years of optimization, there are still some problems, including, for example:

1. The sample needs to be filtered. In case that the sample contains insoluble particles or substances with higher viscosity, if they are left untreated, the carrier would be blocked, so clean-up is required to continue production. In serious cases, the carrier cannot continue to be used, and failure to clean up in time may cause damage to apparatuses.

2. The production process takes a long time. Filtration and concentration of the sample take a relatively long time. Although there are now integrated solutions for filtration and concentration, it still takes a longer time, and the stability of the treatment process is poor.

3. The service life of the carrier is short. In order to improve efficiency, generally the sample is pressurized to flow through the carrier, thus having impacting and squeezing effects on the carrier. The carrier may be broken to a certain extent, reducing the number of times it can be reused.

4. Apparatus loss is large. As the sample is pressurized to flow through the carrier, it not only has impacting and squeezing effects on the carrier, but also has the same effects on the apparatus. To prevent the carrier from flowing with the liquid, a porous support medium must be used below the carrier, while the broken carrier and insoluble particles in the sample may block the support medium. As the apparatus is used over a long period of time, the efficiency of the apparatus gradually decreases until the apparatus has to be abandoned.

SUMMARY OF THE INVENTION

In one aspect, the present invention provides an automatic purification system utilizing magnetic particles, comprising:

1) a first container module, the first container module comprising:

a first container, the first container is provided with a first container liquid inlet at an upper part thereof, and is provided with a first container liquid outlet at a bottom part thereof; and a first magnetic field supply device provided outside the first container; and 2) a system controller module, the system controller module is capable of generating a variable magnetic field inside the first container by controlling the first magnetic field supply device.

In an embodiment, the first magnetic field supply device comprises a first rotating device, a first cantilever and a first permanent magnet, and the first rotating device is capable of controlling the rotation of the first permanent magnet around the first container through the first cantilever.

In an embodiment, the first bracket is provided with a distance adjusting device for adjusting the position of the first permanent magnet so as to be close to or away from the first container.

In an embodiment, the rotation and/or position of the first permanent magnet is controlled by the system controller module through the first rotating device, so as to generate a variable magnetic field inside the first container.

In an embodiment, the first magnetic field supply device comprises a first electromagnet module provided around the outside of the first container.

In an embodiment, the first electromagnet module comprises at least one electromagnet set. Preferably, each of the at least one electromagnet set comprises at least 3 electromagnets provided horizontally.

In an embodiment, whether each of the electromagnets is energized or not and/or the intensity of energization is independently controlled by the system controller module, so that a variable magnetic field can be generated inside the first container. Preferably, the system controller module realizes the generation of a rotating variable magnetic field inside the first container by controlling the alternate energizing and de-energizing of the electromagnets.

In an embodiment, the first container inlet is provided with a first automatic liquid inlet device, the first container outlet is provided with a first container liquid outlet valve, and the liquid inlet selection of the first automatic liquid inlet device as well as the opening and closing of the first container liquid outlet valve are controlled by the system controller module.

In an embodiment, a magnetic shielding layer is provided between the first container and the magnetic field supply device, and the magnetic shielding amount of the magnetic shielding layer is controlled by the system controller module.

In an embodiment, the first container liquid inlet is capable of rinsing the inner wall of the container by means of dispersed liquid outlet, rotating liquid outlet and multi-site liquid outlet.

In an embodiment, the automatic purification system further comprises a second container module, the second container module comprising: a second container, the second container is provided with a second container liquid inlet at an upper part thereof, and is provided with a second container liquid outlet at a bottom part thereof; and a second magnetic field supply device provided outside the second container, wherein the second container module is smaller in overall scale than the first container system.

In an embodiment, the first container liquid outlet valve is connected to the second container liquid inlet. In another embodiment, the first container liquid outlet valve is connected to an automatic liquid discharge device, and the automatic liquid discharge device, under the control of the system controller module, selects to discharge the solution into a waste liquid collecting container or the second container.

In an embodiment, the second magnetic field supply device comprises a second rotating device, a second cantilever and a second permanent magnet, and the second rotating device is capable of controlling the rotation of the second permanent magnet around the second container through the second cantilever.

In an embodiment, the second cantilever is provided with a distance adjusting device for adjusting the position of the second permanent magnet so as to be close to or away from the second container.

In an embodiment, the rotation and/or position of the second permanent magnet is controlled by the system controller module through the second rotating device, so as to generate a variable magnetic field inside the second container.

In an embodiment, the second magnetic field supply device comprises a second electromagnet module provided around the second container.

In an embodiment, the second electromagnet module comprises at least one electromagnet set. Preferably, each of the at least one electromagnet set comprises at least 3 electromagnets provided horizontally.

In an embodiment, whether each of the electromagnets is energized or not and/or the intensity of energization is independently controlled by the system controller module, so that a variable magnetic field can be generated inside the second container.

In an embodiment, the system controller module realizes the generation of a rotating variable magnetic field inside the second container by controlling the alternate energizing and de-energizing of the electromagnets.

In an embodiment, a magnetic shielding layer is provided between the second container and the magnetic field supply device, and the magnetic shielding amount of the magnetic shielding layer is controlled by the system controller module.

In an embodiment, the first container is a fermentation tank. Preferably, the fermentation tank is further equipped with a heating device and/or a venting device and/or a parameter detecting device.

In an embodiment, the automatic purification system is further provided with a plurality of solution containers for storing one or more selected from a magnetic particle suspension, a sample solution, an impurities-washing solution, an eluting solution, a decontaminating solution, and a regenerating solution.

In an embodiment, the automatic purification system is further provided with a plurality of collecting containers for collecting outflows of different components.

In an embodiment, the second container liquid inlet is provided with a second automatic liquid inlet device for selecting a solution to be input into the second container under the control of the system controller module.

In an embodiment, the system controller module comprises a processor and a storage device. Preferably, the storage device stores a program for controlling the automatic operation of the automatic purification system. Preferably, the system control module comprises a computer system.

In another aspect, the present invention provides a method for purifying a target component from a biological sample, comprising the step of contacting the biological sample containing the target component with magnetic particles capable of specifically binding the target component inside the first container in the foregoing automatic purification system.

In an embodiment, the biological sample is a cell culture liquid or a microbial fermentation broth.

In an embodiment, the cell culture liquid or microbial fermentation broth is formed in situ by culturing cells or microbes in the first container, respectively.

In an embodiment, the target component is a biomolecule. Preferably, the biomolecule is a protein or a nucleic acid. Preferably, the protein is an antibody.

In an embodiment, the magnetic particles are comprised of a paramagnetic magnetic core and a coating material.

In an embodiment, the main component of the paramagnetic magnetic core is $Fe_2O_3$ or a mixture of $Fe_2O_3$ and $Fe_3O_4$.

In an embodiment, the magnetic particles have a particle diameter of 100 nm to 200 μm.

In another aspect, the present invention provides a method for breaking cells or bacteria, comprising:

Contacting the cells or bacteria with magnetic particles inside the first container in the foregoing automatic purification system, and Controlling the first magnetic field supply device by the system controller module of the automatic purification system to enhance the magnetic field strength inside the first container, so that the cells or bacteria are broken by the magnetic particles.

The volume of the first container is generally in a range of 200 mL to 50 L.

The magnetic field supply device may be a permanent magnet or a triggering magnet. The permanent magnet may be a natural or artificial magnet. The artificial magnet may be a rare earth permanent magnetic material (neodymium iron boron $Nd_2Fe_{14}B$), a samarium cobalt (SmCo), an aluminum nickel cobalt (AlNiCo), a ferrite permanent magnetic material (Ferrite), and the like.

The triggering magnet can change from non-magnetic to magnetic under certain conditions, such as a magnetizer, an electromagnet, and the like.

The main component of the magnetic particles is $Fe_3O_4$ or a mixture of $Fe_2O_3$ and $Fe_3O_4$. In the mixture of $Fe_2O_3$ and $Fe_3O_4$, the mixing ratio of $Fe_2O_3$ and $Fe_3O_4$ may be 1:20 to 1:1.

The magnetic particles have a specific saturation magnetization of >60 eum/g.

The magnetic particles may be coated with a single layer or multiple layers of materials, and the coating materials include, but are not limited to, silica, agarose, polystyrene, polyglycidyl methacrylate, polyhydroxyethyl methacrylate, and polystyrene-glycidyl methacrylate.

The magnetic particles have a ligand on the exterior thereof capable of identifying a specific molecule, which can identify the specific molecule through various ways such as ionic interaction, Van der Waals force, hydrophobic force, hydrogen bonding, coordination bonding, structural force, and the like, not limited thereto.

The ligand may be a magnetic core self-contained ligand, or a coating material self-contained ligand, or a ligand may be added to the magnetic core or the coating material thereof.

The ligand addition method can be selected from the following methods: chemical bonding, ionic interaction, Van der Waals force, hydrophobic force, hydrogen bonding, coordination bonding, structural force, and the like.

The magnetic field supply device is capable of providing a magnetic field strength in a range between 0.1 T-$10^4$ T.

When there are at least 3 electromagnets, rotation of the magnetic field can be realized without the rotating device, that is, the rotating magnetic field can be realized by the alternate energizing sequence of the electromagnets. The energizing sequence of the electromagnets is determined by the direction of rotation.

When the first or second container is large in volume, one or more sets of magnetic field supply devices can be added to the outside of the container.

The valve provided at the bottom part of the first or second container can be a pinch valve, an electromagnetic valve, a butterfly valve, a column valve, a ball valve, an angle valve, and the like.

The automatic purification device can form multiple sets of cascades, and in case of multiple sets of cascades, there can be only one set of liquid inlet and outlet devices. In case of multiple sets of cascades, a lower stage container can be directly connected behind the liquid outlet valve of an upper stage container.

The automatic purification apparatus of the present application utilizes the characteristic that paramagnetic particles have a magnetic response under a magnetic field, and separates and purifies the corresponding molecules according to a specific identifying region carried on the magnetic particles.

In the present application, a mixing process of magnetic particles with a solution to be treated is utilized to achieve the purpose of binding a specific binding region on the magnetic particles to a component to be separated. Because of the higher tolerance to insoluble particles and substances of high viscosity, the sample pretreatment step in conventional method is omitted, thus time, labor and cost are saved. Since magnetic particles are not impacted or squeezed in the process of mixing the magnetic particles and the sample, the service life of the magnetic particles is much longer than that of a conventional carrier, and likewise, the service life of the apparatus is also much longer than that of a conventional apparatus.

The present application realizes an enrichment function by utilizing the magnetic response characteristic of magnetic particles. Even when the concentration of a component to be separated is relatively low, by means of the function that magnetic particles aggregate under a magnetic field, the component bound to the magnetic particles is concentrated in one region under the magnetic field, thus the enrichment function is realized.

The present application realizes a large-volume self-blending function by utilizing the magnetic response characteristic of magnetic particles. In the process of mixing the magnetic particles and the sample, there is no need to shock or shake the whole set of apparatus, and internal blending is realized through regular movement of the magnetic particles under the magnetic field.

DETAILED DESCRIPTION OF THE PREFERRED EMBODIMENTS

The present invention is explained in more detail below with reference to specific examples and accompanying drawings.

Figure 1:
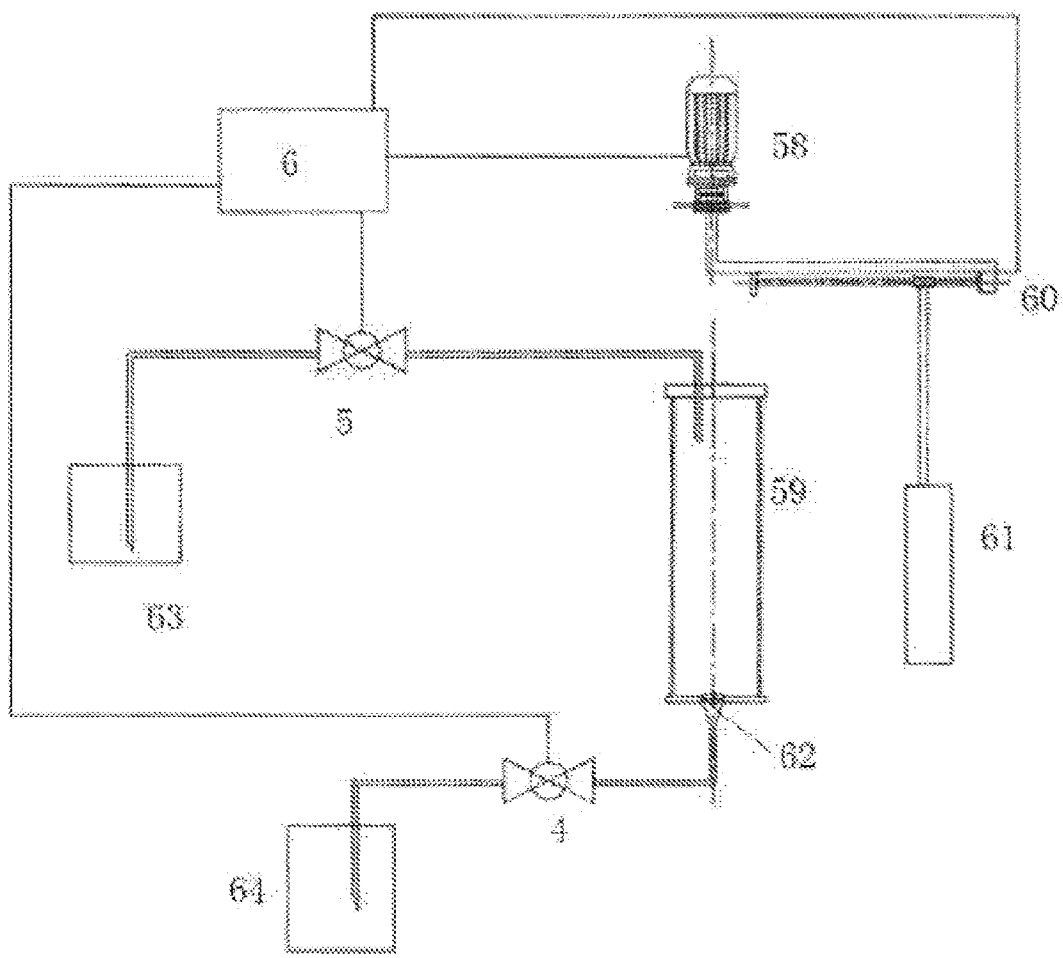
FIG. 1 is a schematic view of an embodiment of an automatic purification system for mixing magnetic particles with a sample solution.

FIG. 1 shows an embodiment in which a permanent magnet was used to generate a variable magnetic field (or a rotating magnetic field) inside a container. In this embodiment, a solution inside a sample solution container 63 could be added to a container 59 through an automatic liquid inlet device 5. At the bottom part of the container 59 was provided a valve 62, which was connected to a waste liquid collecting container 64 through an automatic liquid discharge device 4. A rotating motor 58 was provided above the container 59. The rotating motor 58 had a cantilever 60 provided with a screw rod, and one end of a magnet 61 at the outside of the container 59 was connected to the cantilever 60. A controller 6 was connected with and controlled the rotating motor 58, the cantilever 60, the automatic liquid inlet device 5, the automatic liquid discharge device 4 and the valve 62. Due to the existence of the screw rod structure, the magnet 61 could move along the cantilever 60, so as to be close to or away from the container 59 in position. When the rotating motor 58 rotated, the magnet 61 was driven to rotate along the outside of the container 59 to generate a rotating magnetic field inside the container 59. At the same time, the controller 6 could control the magnet 61 to be close to or away from the container 59 through the cantilever 60, thus producing a change in magnetic field strength inside the container 59.

EXAMPLE 1

Mixing of Magnetic Particles and Sample Solution Inside a 200 mL Container

The following steps were used in operation:

1. A 10 mL suspension of magnetic particles(magnetic particles: aq. 10% ethanol=1:1) was added to a 200 mL container 59 through the controller 6 using the automatic liquid inlet device 5;

2. The cantilever 60 was adjusted through the controller 6, such that the magnet 61 was close to an outer wall of the container 59, and the magnetic particles adsorbed to the inner wall of the container 59;

3. The valve 62 at the bottom part of the container 59 was opened through the controller 6, and the 10% ethanol solution was discharged from the container 59 through the controller 6 using the automatic liquid discharge device 4;

4. The valve 62 was closed through the controller 6;

5. A 150 mL sample solution was added to the container 59 through the controller 6 using the automatic liquid inlet device 5;

6. The controller 6 controlled the rotating motor 58 to start rotating at a speed of 50 rpm/min, and controlled the magnet 61 to reciprocate on the cantilever 60 at the same time; and 7. The magnetic particles were driven by the magnet 61 to move circumferentially inside the container 59 and thoroughly mixed with the sample solution.

The volume of the container 59 was determined according to sample size, and generally the volume of the container 59 was approximately 1-3 times of the sample size.

The amount of magnetic particles used was determined according to the concentration of ligand on the magnetic particles and the amount of component to be separated in the sample. Generally, the calculation method was:

$$V=a*M/m$$

M: mass of the component to be separated (mg)
m: ligand concentration on the magnetic particles (mg/mL)
V: amount of the magnetic particles used (mL)
a: human interference coefficient, generally 1-3

The magnet 61 was a permanent magnet, the magnetic field strength was selected in a range of 0.1T-2T, and the rotating speed of the rotating motor 58 was selected in a range of 10-1000 rpm/min.

Figure 2:
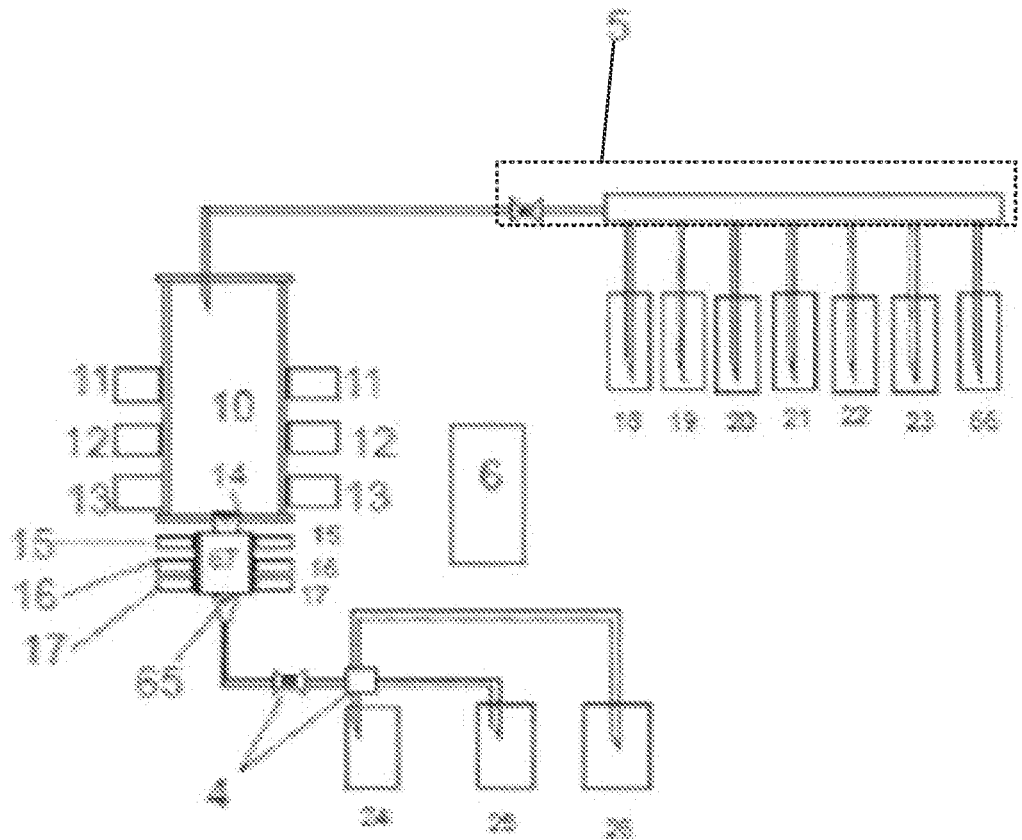
FIG. 2 is a schematic view of an embodiment of an automatic purification system provided with a cascade of containers.
Figure 3:
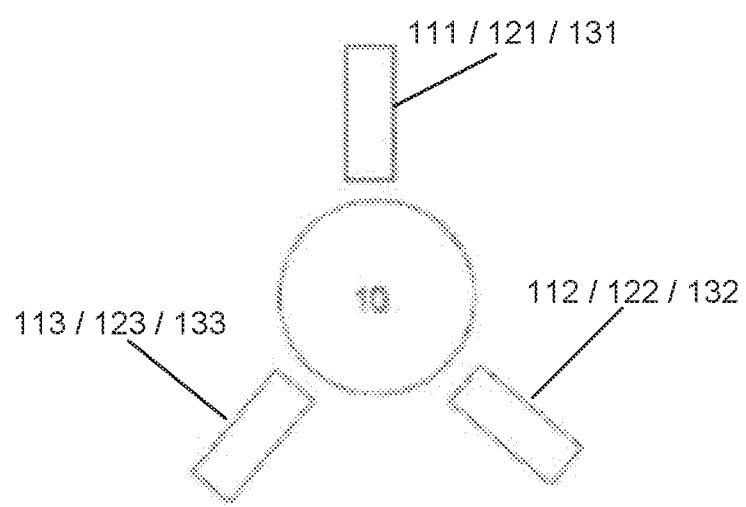
FIG. 3 is a schematic view showing an arrangement of an electromagnet set composed of three electromagnets.

FIG. 2 shows an embodiment in which a variable magnetic field is generated inside a container using an electromagnet. In this embodiment, the contents of a magnetic particle container 18, an equilibrium solution container 19, an impurities-washing solution container 20, an elating solution container 21, a sample solution container 22, a regenerating solution container 23, and an aq. 10% ethanol solution container 66 could enter a container 10 through an automatic liquid inlet device 5. Three electromagnet sets 11, 12 and 13 were layered at the periphery of the container 1.0. Each electromagnet set comprised three electromagnets arranged horizontally around the container 10 at substantially equal distances. FIG. 3 provides a schematic view of an electromagnet set which can represent any of the three electromagnet sets 11, 12, and 13. In particular, the electromagnet set shown in FIG. 3 can represent the electromagnet set 11 which comprised three electromagnets 111, 112 and 113, the electromagnet set 12 which comprised three electromagnets 121, 122 and 123, or the electromagnet set 13 which comprised three electromagnets 131, 132 and 133. The electromagnet 121 was arranged below the electromagnet 111, and the electromagnet 131 was arranged below the electromagnet 121; the electromagnet 122 was arranged below the electromagnet 112, and the electromagnet 132 was arranged below the electromagnet 122; the electromagnet 123 was arranged below the electromagnet 113, and the electromagnet 133 was arranged below the electromagnet 123. A valve 14 was provided at the bottom part of the container 10 and cascaded to another smaller container 67. Likewise, three electromagnet sets 15, 16 and 17 were layered at the periphery of the container 67. The arrangement of these electromagnet sets was similar to that of the electromagnet sets 11, 12 and 13. A valve 65 was provided at the bottom part of the container 67, and was connected through an automatic liquid discharge device 4 to a waste liquid collecting container 24, an eluent collecting container 25 and a magnetic particle recovering container 26, respectively. A controller 6 was connected with and controlled the automatic liquid inlet device 5, the valve 14, the valve 65 and the automatic liquid discharge device 4. The controller 6 further controlled the energization and de-energization of the electromagnets of the respective electromagnet sets 11, 12, 13. 15, 16 and 17, respectively, so as to generate a variable magnetic field (or a rotating magnetic field) inside the containers 10 and 67.

EXAMPLE 2

Purification of a Target Protein in a 15 L Sample by Separation

The following steps were used in operation:

1. Closing the valves 14 and 65 through the controller 6;

2. Adding a 1 L suspension of magnetic particles (the particle surface having a ligand bound to the target protein) (magnetic particles: aq. 10% ethanol solution=1:1) to a 20 L container 10 through the controller 6 using the automatic liquid inlet device 5;

3. Simultaneously energizing the electromagnet sets 11, 12 and 13 through the controller 6 to generate a magnetic field, such that the magnetic particles were adsorbed to the inner wall of the container 10;

4. Opening the valves 14 and 65 through the controller 6, and discharging the 10% ethanol solution through the controller 6 using the automatic liquid discharge device 4;

5. Closing the valves 14 and 65 through the controller 6;

6. Controlling, through the controller 6, the automatic liquid inlet device 5 to add a 10 L equilibrium solution to the container 10;

7. Controlling, through the controller 6, the electromagnet sets 11, 12 and 13 to start energizing and de-energizing in the following sequence: 131-122-113-132-123-111-133-121-112-131-122-. . . , such that the magnetic particles moved in swirled form;

8. Simultaneously energizing the electromagnet sets 11, 12 and 13 through the controller 6 to generate a magnetic field, such that the magnetic particles were adsorbed to the inner wall of the container 10;

9. Opening the valves 14 and 65 through the controller 6 and discharging a waste liquid;

10. Adding a 15 L sample solution to the container 10 through the controller 6 using the automatic liquid inlet device 5;

11. Controlling, through the controller 6, the electromagnet sets 11, 12 and 13 to start energizing in the following sequence: 131-122-113-132-123-111-133-121-112-131-122-. . . , such that the magnetic particles moved in swirled form;

12. Allowing the magnetic particles to move in swirled form for 20 min to 2 h to ensure the ligand on the magnetic particles being sufficiently bound to the component to be separated in the sample;

13. Simultaneously energizing the electromagnet sets 11, 12 and 13 through the controller 6 to generate a magnetic field, such that the magnetic particles were adsorbed to the inner wall of the container 10;

14. Opening the valves 14 and 65 through the controller 6 and discharging a waste liquid;

15. De-energizing the electromagnet sets 11, 12 and 13 through the controller 6, such that the magnetic field disappeared;

16. Adding a 0.8 L impurities-washing solution by rinsing to the container 10 through the controller 6 using the automatic liquid inlet device 5, such that the magnetic particles adsorbed to the inner wall of the container 10 were rinsed into the container 67 with a volume of 1 L;

17. Controlling, through the controller 6, the electromagnet sets 15, 16 and 17 to start energizing and de-energizing in the following sequence: 171-162-153-172-163-151-173-161-152-171-162-. . . , such that the magnetic particles moved in swirled form;

18. Allowing the magnetic particles to move in swirled form for 5 min to 1 h,

19. Simultaneously energizing the electromagnet sets 15, 16 and 17 through the controller 6 to generate a magnetic field, such that the magnetic particles were adsorbed to the inner wall of the container 67;

20. Opening the valve 65 through the controller 6 and discharging a waste liquid;

21. Adding the impurities-washing solution 1-5 times as needed, and performing steps 16-20 each time;

22. Adding a 750 mL eluting solution to the container 67;

23. Controlling, through the controller 6, the electromagnet sets 15, 16 and 17 to start energizing in the following sequence: 171-162-153-172-163-151-173-161-152-171-162-. . . , such that the magnetic particles moved in swirled form;

24. Allowing the magnetic particles to move in swirled form for 5 min to 1 h;

25. Opening the valve 65 and collecting an eluting solution;

26. Repeating steps 21 to 24 for 1 to 3 times;

27. Adding a 750 mL regenerating solution to the container 67;

28. Controlling, through the controller 6, the electromagnet sets 15, 16 and 17 to start energizing in the following sequence: 171-162-153-172-163-151-173-161-152-171-162-. . . , such that the magnetic particles moved in swirled form;

29. Allowing the magnetic particles to move in swirled form for 5 min to 1 h;

30. Opening the valve 65 and discharging a waste liquid;

31. Repeating steps 27 to 30 for 1 to 3 times;

32. De-energizing the electromagnet sets 15, 16 and 17, such that the magnetic field disappeared;

33. Opening the valve 65;

34. Adding a 100 mL of 10% ethanol solution to the container 67;

35. Collecting an effluent; and

36. Repeating 34 and 35 for 5 times, and collecting all of the magnetic particles.

For the conventional method, it took about 24 to 48 h to purify a 15 L cell culture liquid, while with this automatic purification system, the process of purification to regeneration could be completed within 12 h. The solution used could be, for example, the equilibrium solution: phosphate buffer solution, 0.01-0.1M, pH=5.1-8.2; the impurities-washing solution: phosphate buffer solution, 0.01-0.1M, pH=5.1-8.2; the eluting solution: glycine-hydrochloric acid buffer solution, 0.01-0.1M, pH=1.2-4.5; and the regenerating solution: aq. sodium hydroxide solution, 0.1-0.5M, or aq. 50% isopropanol solution. The target protein in the sample could be for example IgG, and correspondingly, the ligand on magnetic particles was protein A. The electromagnet used could generate a magnetic field strength of 0.5 T to $10^3$ T.

Figure 4:
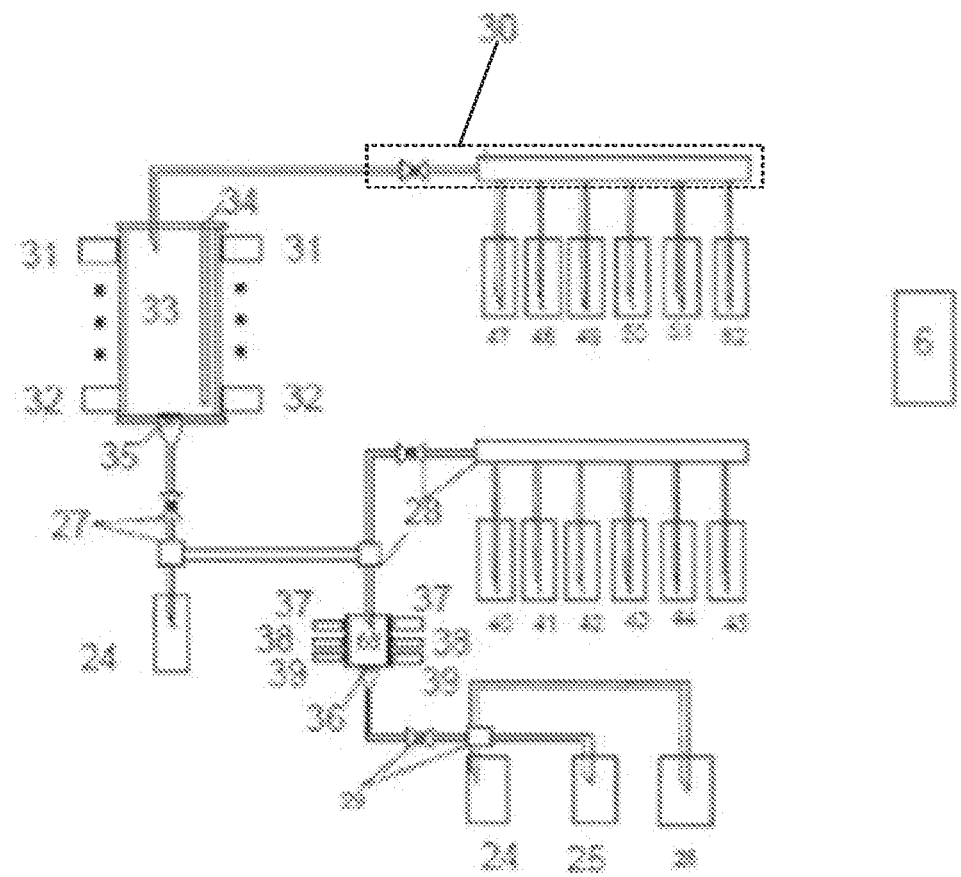
FIG. 4 is a schematic view of an embodiment of an automatic purification system using a fermentation tank as a first container.
Figure 5:
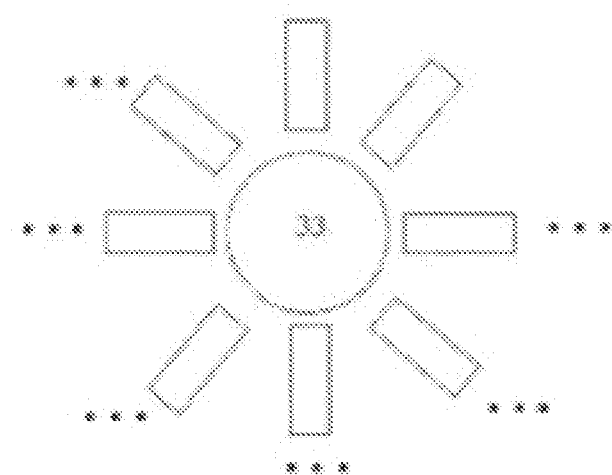
FIG. 5 is a schematic view showing an arrangement of an electromagnet set composed of a plurality of electromagnets.

FIG. 4 shows an embodiment using a fermentation tank. The contents of a culture medium container 47, a magnetic particle container 48, an impurities-washing solution container 49, an inducer container 50, and other containers 51, 52 could enter a fermentation tank 33 through an automatic liquid inlet device 30. The fermentation tank 33 was provided with a fermentation tank accessory 34 such as a heating device, a real-time monitoring device, and the like. At the outside of the fermentation tank 33 were provided with a plurality of electromagnet sets 31 . . . 32, and the arrangement of each electromagnet set could be seen in FIG. 5. A valve 35 was provided at the bottom part of the fermentation tank 33 and connected to a waste liquid collecting container 24 or a container 68 through an automatic liquid discharge device 27. The contents of an impurities-washing solution container 40, an eluting solution container 41, a decontaminating solution container 42, a regenerating solution container 43, an aq. 10% ethanol solution container 44, an additional container 45, and the fermentation tank 33 could enter the container 68 through an automatic liquid inlet device 28. At the outside of the container 68 were provided three electromagnet sets 37, 38 and 39. A valve 36 was provided at the bottom part of the container 68 and connected to the waste liquid collecting container 24, the eluent collecting container 25 and the magnetic particle recovering container 26 through an automatic liquid discharge device 29. The controller 6 was connected with and controlled the automatic liquid inlet device 30, the automatic liquid discharge device 27, the automatic liquid inlet device 28, the automatic liquid discharge device 29, the valve 35 and the valve 36. At the same time, the controller 6 also controlled the respective electromagnets to generate variable magnetic fields inside the fermentation tank 33 and inside the container 68 through energization or de-energization and current intensity.

EXAMPLE 3

The Process of Culturing and Purification in a 50 L Fermentation Tank

The culturing and purification of the target product could be completed by the following operations:

1. Cleaning and sterilizing the 50 L fermentation tank 33 and corresponding pipelines;
2. Adding a 45 L sterile culture medium and a 1 L magnetic particles to the 50 L fermentation tank 33;
3. Controlling, through the controller 6, the electromagnet sets 31 . . . 32 to turn on by reciprocating up and down spirally, such that the magnetic particles swirled slowly;
4. Maintain the temperature of the culture medium at 20 to 40° C. by the heating device in the fermentation tank accessory 34;
5. Inoculating bacteria;
6. Culturing for 24 to 200 h;
7. Monitoring, by the fermentation tank accessory 34 in real time, parameters of the medium, such as contents of dissolved oxygen and glucose and other parameters, to determine the entry into a log phase;
8. Adding an inducer;
9. Monitoring, by the fermentation tank accessory 34 in real time, parameters of the medium, such as contents of dissolved oxygen and glucose and other parameters, to determine the entry into a stable phase, and turning off the heating device;
10. Increase input powers of the electromagnet sets 31 . . . 32, such that the magnetic particles swirled violently;
11. Maintaining the violent swirling movement for 15 min to 1 h to break thalli;
12. Reducing input powers of the electromagnet sets 31 . . . 32 to form a slow swirling movement and maintaining for 15 min to 10 h;
13. Controlling, through the controller 6, all of the electromagnet sets 31 . . . 32 to be energized, such that the magnetic particles were adsorbed to the inner wall of the fermentation tank 33;
14. Opening the valve 35 through the controller 6;
15. Discharging the culture medium through the automatic liquid discharge device 27;
16. De-energizing all of the electromagnet sets 31 . . . 32;
17. Adding a 1 L impurities-washing solution through the automatic liquid inlet device 30 to rinse the inner wall of the fermentation tank 33, such that the magnetic particles fell off and entered into the 1.5 L container 68 through the automatic liquid discharge device 27 (and the automatic liquid inlet device 28);
18. Controlling the electromagnet sets 37, 38 and 39 to turn on by reciprocating up and down spirally, such that the magnetic particles swirled slowly;
19. Maintaining for 15 min to 1 h;
20. Energizing all of the electromagnet sets 37, 38 and 39, such that the magnetic particles were adsorbed to the inner wall of the container 68;
21. Opening the valve 36 through the controller 6;
22. Discharging the solution into the waste liquid collecting container 24 through the automatic liquid discharge device 29;
23. Closing the valve 36 through the controller 6;
24. Adding a 1 L impurities-washing solution through the automatic liquid inlet device 30 to rinse the inner wall of the fermentation tank 33, and entering into the 1.5 L container 68 through the automatic liquid discharge device 27 (and the automatic liquid inlet device 28);
25. Allowing the electromagnet sets 37, 38 and 39 to turn on by reciprocating up and down spirally, such that the magnetic particles swirled slowly;
26. Maintaining for 15 min to 1 h;
27. Energizing all of the electromagnet sets 37, 38 and 39, such that the magnetic particles were adsorbed to the inner wall of the container 68;
28. Opening the valve 36;
29. Discharging the solution into the waste liquid through the automatic liquid discharge device 29;
30. Closing the valve 36;
31. Repeating steps 24 to 30 for 1 to 5 times as needed;
32. De-energizing all of the electromagnet sets 37, 38 and 39;
33. Adding a 1 L eluting solution to the container 68 through the automatic liquid inlet device 28;
34. Allowing the electromagnet sets 37, 38 and 39 to turn on by reciprocating up and down spirally, such that the magnetic particles swirled slowly;
35. Maintaining for 15 min to 1 h;
36. Energizing all of the electromagnet sets 37, 38 and 39, such that the magnetic particles were adsorbed to the inner wall of the container 68;
37. Opening the valve 36;
38. Discharging the solution into the eluent collecting container 25 through the automatic liquid discharge device 29;
39. Closing the valve 36;
40. Repeating steps 32 to 39 for 1 to 5 times;
41. De-energizing all of the electromagnet sets 37, 38 and 39;
42. Adding a 1 L decontaminating solution to the container 68 through the automatic liquid inlet device 28;
43. Allowing the electromagnet sets 37, 38 and 39 to turn on by reciprocating up and down spirally, such that the magnetic particles swirled slowly;
44. Maintaining for 15 min to 1 h;
45. Energizing all of the electromagnet sets 37, 38 and 39, such that the magnetic particles were adsorbed to the inner wall of the container 68;
46. Opening the valve 36;
47. Discharging the solution into the waste liquid collecting container 24 through the automatic liquid discharge device 29;
48. Closing the valve 36;
49. Repeating steps 41 to 48 for 1 to 5 times as needed;
50. De-energizing all of the electromagnet sets 37, 38 and 39;
51. Adding a 1 L regenerating solution to the container 68 through the automatic liquid inlet device 28;
52. Allowing the electromagnet sets 37, 38 and 39 to turn on by reciprocating up and down spirally, such that the magnetic particles swirled slowly;
53. Maintaining for 15 min to 1 h;
54. Energizing all of the electromagnet sets 37, 38 and 39, such that the magnetic particles were adsorbed to the inner wall of the container 68;
55. Opening the valve 36;
56. Discharging the solution into the waste liquid collecting container 24 through the automatic liquid discharge device 29;

57. De-energizing all of the electromagnet sets 37, 38 and 39;

58. Adding a 1 L aq. 10% ethanol solution to the container 68 through the automatic liquid inlet device 28, such that the magnetic particles were rinsed and fell off the container wall, and entered into the magnetic particle collecting container 26 through the automatic liquid discharge device 29; and 59. Repeating step 58.

The impurities-washing solution used could be for example, 20 mM imidazole, 50 mM Tris-HCl and 150 mM NaCl; the eluting solution used could be for example, 250 mM imidazole, 50 mM Tris-HCl and 150 mM NaCl; the decontaminating solution used could be for example, aq. sodium hydroxide solution, and aq. 1-4 M or 50% isopropanol solution; and the regenerating solution used could be for example, 50 mM $NiSO_4$. When the inducibly-expressed protein in the fermentation tank was a protein with His tag, the ligand on the magnetic particles could be for example NTA—Ni.

It should be understood by those skilled in the art that the features of the embodiments disclosed in this application may be combined, rearranged, etc. to obtain other embodiments within the scope of the present invention, and various other changes, omissions, and additions could may also be made without departing from the spirit and scope of the present invention.

The invention claimed is:

1. An automatic purification system utilizing magnetic particles, comprising:
   1) a first container module, the first container module comprising:
      a first container, the first container provided with a first container liquid inlet at an upper part thereof and a first container liquid outlet at a bottom part thereof; and
      a first magnetic field supply device provided outside the first container;
   2) a system controller module, the system controller module capable of generating a variable magnetic field inside the first container by controlling the first magnetic field supply device;
      wherein the first container liquid inlet is provided with a first automatic liquid inlet device, the first container liquid outlet is provided with a first container liquid outlet valve, and a liquid inlet selection of the first automatic liquid inlet device as well as the opening and closing of the first container liquid outlet valve are controlled by the system controller module; and
   3) a second container module comprising:
      a second container, the second container provided with a second container liquid inlet at an upper part thereof, a second container liquid outlet at a bottom part thereof; and
      a second magnetic field supply device provided outside the second container,
      wherein the second container module is smaller in overall scale than the first container module; and
      wherein the first container liquid outlet valve is connected to the second container liquid inlet, or is connected to an automatic liquid discharge device, and the automatic liquid discharge device, under the control of the system controller module, selects to discharge a solution into a waste liquid collecting container or the second container.

2. The automatic purification system of claim 1, wherein the first magnetic field supply device comprises a first rotating device, a first cantilever and a first permanent magnet, and the first rotating device is capable of controlling the rotation of the first permanent magnet around the first container through the first cantilever; wherein the first cantilever is provided with a distance adjusting device for adjusting the position of the first permanent magnet so as to be close to or away from the first container; wherein the rotation and/or position of the first permanent magnet is controlled by the system controller module through the first rotating device, so as to generate a variable magnetic field inside the first container.

3. The automatic purification system of claim 1, wherein the first magnetic field supply device comprises a first electromagnet module provided around the outside of the first container; wherein the first electromagnet module comprises at least one electromagnet set; wherein each of the at least one electromagnet set comprises at least 3 electromagnets provided horizontally; wherein whether each of the electromagnets is energized or not and/or the intensity of energization is independently controlled by the system controller module, so that the variable magnetic field can be generated inside the first container.

4. The automatic purification system of claim 3, wherein the system controller module realizes the generation of a rotating variable magnetic field inside the first container by controlling the alternate energizing and de-energizing of the electromagnets.

5. The automatic purification system of claim 4, wherein the rotating variable magnetic field is a driving force for a controllable movement of the magnetic particles in the container.

6. The automatic purification system of claim 1, wherein the first container liquid inlet is capable of rinsing the inner wall of the first container.

7. The automatic purification system of claim 1, wherein the second magnetic field supply device comprises a second rotating device, a second cantilever and a second permanent magnet, and the second rotating device is capable of controlling the rotation of the second permanent magnet around the second container through the second cantilever; wherein the second cantilever is provided with a distance adjusting device for adjusting the position of the second permanent magnet so as to be close to or away from the second container; wherein the rotation and/or position of the second permanent magnet is controlled by the system controller module through the second rotating device, so as to generate a variable magnetic field inside the second container.

8. The automatic purification system of claim 1, wherein the second magnetic field supply device comprises a second electromagnet module provided around the second container; wherein the second electromagnet module comprises at least one electromagnet set; wherein each of the at least one electromagnet set comprises at least 3 electromagnets provided horizontally; wherein whether each of the electromagnets is energized or not and/or the intensity of energization is independently controlled by the system controller module, so that a variable magnetic field can be generated inside the second container.

9. The automatic purification system of claim 8, wherein the system controller module realizes the generation of a rotating variable magnetic field inside the second container by controlling the alternate energizing and de-energizing of the electromagnets.

10. The automatic purification system of claim 1, wherein the first container is a fermentation tank.

11. The automatic purification system of claim 1, wherein the automatic purification system is further provided with a plurality of solution containers for storing one or more selected from a magnetic particle suspension, a sample solution, an impurities-washing solution, an eluting solution, a decontaminating solution, and a regenerating solution.

12. The automatic purification system of claim 1, wherein the automatic purification system is further provided with a plurality of collecting containers for collecting outflows of different components.

13. The automatic purification system of claim 1, wherein the second container liquid inlet is provided with a second automatic liquid inlet device for selecting a solution to be input into the second container under the control of the system controller module.

14. The automatic purification system of claim 1, wherein the system controller module comprises a processor and a storage device, wherein the storage device stores a program for controlling the automatic operation of the automatic purification system; or the system controller module comprises a computer system.

15. A method for purifying a target component from a biological sample, comprising contacting the biological sample containing the target component with magnetic particles capable of specifically binding the target component inside a first container in an automatic purification system, wherein the automatic purification system utilizes magnetic particles and comprises:
   1) a first container module, the first container module comprising:
   the first container, the first container provided with a first container liquid inlet at an upper part thereof and a first container liquid outlet at a bottom part thereof; and
   a first magnetic field supply device provided outside the first container;
   2) a system controller module, the system controller module capable of generating a variable magnetic field inside the first container by controlling the first magnetic field supply device:
   wherein the first container liquid inlet is provided with a first automatic liquid inlet device, the first container liquid outlet is provided with a first container liquid outlet valve, and a liquid inlet selection of the first automatic liquid inlet device as well as the opening and closing of the first container liquid outlet valve are controlled by the system controller module; and
   3) a second container module comprising:
   a second container, the second container provided with a second container liquid inlet at an upper part thereof, a second container liquid outlet at a bottom part thereof; and
   a second magnetic field supply device provided outside the second container,
   wherein the second container module is smaller in overall scale than the first container module; and
   wherein the first container liquid outlet valve is connected to the second container liquid inlet, or is connected to an automatic liquid discharge device, and the automatic liquid discharge device, under the control of the system controller module, selects to discharge a solution into a waste liquid collecting container or the second container.

16. The method of claim 15, wherein the first magnetic field supply device comprises a first rotating device, a first cantilever and a first permanent magnet, and wherein the second magnetic field supply device comprises a second rotating device, a second cantilever and a second permanent magnet.

17. The method of claim 15, wherein the first magnetic field supply device comprises a first electromagnet module provided around the outside of the first container, and wherein the second magnetic field supply device comprises a second electromagnet module provided around the second container.

18. A method for breaking cells or bacteria, comprising:
   contacting the cells or bacteria with magnetic particles inside a first container in an automatic purification system, wherein the automatic purification system comprises:
   1) a first container module, the first container module comprising:
   the first container, the first container provided with a first container liquid inlet at an upper part thereof and a first container liquid outlet at a bottom part thereof; and
   a first magnetic field supply device provided outside the first container;
   2) a system controller module, the system controller module capable of generating a variable magnetic field inside the first container by controlling the first magnetic field supply device:
   wherein the first container liquid inlet is provided with a first automatic liquid inlet device, the first container liquid outlet is provided with a first container liquid outlet valve, and a liquid inlet selection of the first automatic liquid inlet device as well as the opening and closing of the first container liquid outlet valve are controlled by the system controller module; and
   3) a second container module comprising:
   a second container, the second container provided with a second container liquid inlet at an upper part thereof, a second container liquid outlet at a bottom part thereof; and
   a second magnetic field supply device provided outside the second container,
   wherein the second container module is smaller in overall scale than the first container module;
   wherein the first container liquid outlet valve is connected to the second container liquid inlet, or is connected to an automatic liquid discharge device, and the automatic liquid discharge device, under the control of the system controller module, selects to discharge a solution into a waste liquid collecting container or the second container; and
   wherein the system controller module of the automatic purification system controls the first magnetic field supply device to enhance the magnetic field strength inside the first container, so that the cells or bacteria are broken by the magnetic particles.

19. The method of claim 18, wherein the first magnetic field supply device comprises a first rotating device, a first cantilever and a first permanent magnet, and wherein the second magnetic field supply device comprises a second rotating device, a second cantilever and a second permanent magnet.

20. The method of claim 18, wherein the first magnetic field supply device comprises a first electromagnet module provided around the outside of the first container, and wherein the second magnetic field supply device comprises a second electromagnet module provided around the second container.

\* \* \* \* \*